United States Patent
Preissman (10) Patent No.: US 8,206,443 B2
(45) Date of Patent: Jun. 26, 2012

(54) FAIL-SAFE SILICONE BREAST IMPLANT DELIVERY DEVICE

(75) Inventor: Howard E. Preissman, Stuart, FL (US)

(73) Assignee: Keller Medical, Inc., Stuart, FL (US)

( * ) Notice: Subject to any disclaimer, the term of this patent is extended or adjusted under 35 U.S.C. 154(b) by 0 days.

(21) Appl. No.: 12/850,518

(22) Filed: Aug. 4, 2010

(65) Prior Publication Data

US 2011/0035003 A1  Feb. 10, 2011

Related U.S. Application Data

(63) Continuation-in-part of application No. 12/387,215, filed on Apr. 29, 2009.

(51) Int. Cl.
*A61F 2/12* (2006.01)
(52) U.S. Cl. .................................. 623/8; 623/7
(58) Field of Classification Search .................... 623/7–8
See application file for complete search history.

(56) References Cited

U.S. PATENT DOCUMENTS

| | | | |
|---|---|---|---|
| 2,935,241 A | 5/1960 | Brady | |
| 3,138,821 A | 6/1964 | Macciocchi et al. | |
| 3,156,240 A | 11/1964 | Harrison et al. | |
| 4,035,850 A | 7/1977 | Cresswall | |
| 4,955,906 A * | 9/1990 | Coggins et al. | 623/8 |
| 5,052,554 A | 10/1991 | Leonard | |
| 5,201,779 A * | 4/1993 | Shiao | 606/91 |
| 5,723,006 A | 3/1998 | Ledergerber | |
| 6,238,799 B1 | 5/2001 | Opolski | |
| 6,383,191 B1 | 5/2002 | Zdeblock et al. | |
| 6,790,238 B1 * | 9/2004 | Martin | 623/36 |
| 6,866,936 B2 | 3/2005 | Opolski | |
| 7,137,995 B2 | 11/2006 | Studin | |
| 2006/0184100 A1 | 8/2006 | Studin | |
| 2007/0276484 A1 | 11/2007 | Abell et al. | |
| 2008/0241212 A1 | 10/2008 | Moses et al. | |
| 2009/0204107 A1 | 8/2009 | Keller et al. | |

FOREIGN PATENT DOCUMENTS

CN  201076483  6/2008

* cited by examiner

*Primary Examiner* — Thomas J Sweet
*Assistant Examiner* — Seema Swaminathan
(74) *Attorney, Agent, or Firm* — Dickstein Shapiro LLP; Mark Stirrat (57) ABSTRACT

A tapered sleeve is provided for implant delivery. An implant (e.g., a pre-filled silicone breast implant) is introduced into a large proximal end of the sleeve and extruded into a surgical pocket of minimal access incision size through a small-sized distal end of the device. Sized appropriately to the implant, the sleeve remains intact during implant run-through of the sleeve.

6 Claims, 8 Drawing Sheets

FAIL-SAFE SILICONE BREAST IMPLANT DELIVERY DEVICE

CROSS-RELATED APPLICATION

This application is a continuation-in-part of U.S. patent application Ser. No. 12/387,215, filed Apr. 29, 2009, which is fully incorporated herein by reference.

BACKGROUND

Silicone breast implants were re-approved in the United States in November, 2006, after having been withdrawn from the market. Implant recipients cite safety, scarring, and "natural" look and feel to be the top three indicators in selecting between saline- and silicone-filled implants for breast augmentation. Given that the more natural look and feel offered by silicone is a pre-requisite for many patients, silicone implants have already achieved nearly 50% market share following their return to the market.

But because silicone implants are pre-filled (to alleviate leakage concerns) they have generally required larger access incisions than saline implants. Due to the possibility of visible scars associated with the larger incisions, some patients have remained apprehensive about selecting silicone implants.

An additional consideration that has thus-far weighed against silicone implant selection involves the amount of time required for insertion. Hand manipulation can be time consuming even for a highly-skilled surgical practitioner. The time spent has a direct bearing on the expense of the procedure.

The extent (and nature) of such manipulation also impacts the safety of the procedure. Stated plainly, the poking and pushing required to manually insert a prefilled silicone implant can be quite rough. Indeed, clinical studies have shown that the majority of silicone implant leaks/ruptures are attributable to sharp instrument damage and/or local stress forces exerted on the implant at the time of insertion.

Advances have been made in the construction methods and materials used in silicone breast implants over the last decade (e.g., the introduction of cohesive gels, textured shells, and anatomical shapes). However, little improvement has been made in the method of inserting the implants. That is, until use of the device described in U.S. patent application Ser. No. 12/228,072 to Keller.

The Keller filing describes a device and methods addressing each of the above-referenced issues. It discloses a specially-adapted pastry bag type device for implant introduction. The device enables silicone implant insertion though smaller incisions at dramatically reduced introduction time as compared to the common practice for silicone implant introduction. Likewise, the potential for implant damage has been significantly reduced. By addressing the cited delivery challenges through use of the Keller device, the popularity of silicone-based implants is poised to overtake that of saline-filled counterparts. This scenario is made more likely given ultimate market introduction of the Keller device with improvements as described herein.

SUMMARY

Like the original Keller device, the present invention comprises a truncated conical sleeve. The frustum-shaped device is adapted to receive a silicone breast implant and by squeezing the sleeve and expelling the implant from its smaller end into a tissue pocket. The implant delivery sleeve is constructed of a flexible fabric and similar in size to store-bought pastry bags.

More specifically, since the size of silicone implants may vary in a range from about 150 cc to about 800 cc, the dimensions of the sleeve may vary. A proximal opening sized to fit any implant in this size range and a distal opening sized to fit the smallest implant may be desirable. The distal/tip opening then may be enlarged by trimming the sleeve to provide a larger opening. Indicia may be present on the exterior of the sleeve as a guide for cutting to the proper dimensions. Otherwise, a template or other means may be provided to assist in trimming.

In use, the small end of the delivery sleeve is placed through a skin incision into a tissue pocket and pressure is applied to force the implant from the sleeve into the pocket in use. Such action avoids rough or gross manipulation as required by manual implantation. As such, use of the sleeve makes for a more "gentle" procedure reducing the potential for implant damage and/or adjacent tissue trauma. It also allows the implant to be inserted without touching skin, thereby minimizing the transmission of skin-based flora.

Still further, the small size of the delivery sleeve opening allows the physician flexibility in his/her surgical approach by allowing the access through the inframammary, periareolar, or axillary sites. In all cases, the incision is smaller and less noticeable than otherwise required for inserting silicone implants, thereby diminishing any scarring.

While similarly advantageous in regard to the above, the present invention incorporates additional features and advantages in use as compared to the Keller system.

For instance, the sleeve is advantageously constructed of rip-stop nylon fabric. In such construction, the fabric is advantageously between about ¾ to about 1½ oz weight material per sailmaker's yard. It may be as heavy 2¼ oz or heavier still by the same standard. To offer maximum translucency when wet-out (a feature useful for determining/confirming implant orientation within the sleeve), the fabric is preferably not pigmented. Other material options are possible as well, but the rip-stop nylon offers particular advantages in terms of durability and ease of handling, especially in connection with its use as further described below.

Other constructional features define another optional aspect of the present invention. Specifically, the device is advantageously cut from rip-stop nylon cloth that is adhered along an overlapping seam with double-sided tape. 3M, Inc. offers 5 mill transfer tape that is suitable for this purpose; suitable fabric may be obtained from Challenge Sailcloth, Inc. So constructed, no binding of the fabric edges is required to prevent unraveling or other problems. Cost is utterly minimized, without any compromise in performance.

In fact, definite performance advantages can be realized with this construction. Namely, for constructions in which the sleeve fabric remains unbound at the distal end of the sleeve, the approach offers an inherent safety feature. Sized appropriately to the implant, the distal end of the sleeve remains intact and the implant delivered without incident. However, if the end of the sleeve is undersized relative to the implant (to the extent that damage might occur to the implant if it were forced through the sleeve), the sleeve is configured so that the end of the sleeve fails (i.e., tears, rips or splits) instead. The configuration, specifically, is one in which the end of the sleeve is unreinforced along the cut edge of the aforementioned "rip-stop" fabric.

But, of course, the "rip-stop" designation of the fabric is a term of art. Rip-stop fabric is (typically) a light-weight (often) nylon fabric with interwoven reinforcement threads in a crosshatch pattern. It is woven with coarse, strong warp and filling yarns spaced at intervals to help prevent the spread of tears.

While originally developed for parachutes in which true rip-stop action is critical, the fail-safe performance aspect of the present invention puts the "rip-stop" feature to relative use. The fabric must be relatively strong enough to permit use in passing appropriately-sized implants, but friable when pushing an implant through the sleeve that is oversized relative to the end opening. If the end of the sleeve is not large enough relative to the implant (as originally provided and/or as-trimmed), the fabric (or associated feature) will tear, open or otherwise separate, relieving the stress on the implant being pushed through the distal end opening/aperture of the sleeve. As a result, the implant will be undamaged despite the aggressive use to which it has been subjected. Indeed, extensive testing has proven that implants are generally not damaged when the sleeve is so undersized and such a safety feature is included in the sleeve.

Note, however, that such aggressive use does not necessarily connote misuse. Given experience and developing a certain feel for use of the device, physicians may choose to size the distal opening of the sleeve relatively smaller. (Even smaller than recommended by the guide and training provided by the assignee hereof.) The reason for such action may be to absolutely minimize the size of incision through which an implant is placed. Regardless of the reason, both the patient and surgeon are protected from becoming overly aggressive in this regard by means of the fail-safe feature of the present invention. The physician is offered feedback by the delivery device itself for what is an acceptable level of stress upon the implant. And patient's outcomes can be improved by virtue of protecting implant integrity, when undetectable damage to the implant could otherwise occur.

Accordingly, if running an implant through the sleeve to check size causes a failure of the sleeve, the implant need not be discarded. Rather, another inexpensive sleeve is opened from sterile packaging and trimmed more appropriately for use, and, the implantation procedure can proceed. As such, fail-safe performance advantages are offered by the sleeve construction.

Another type of fail-safe approach is contemplated as well. Specifically, it operates proximal to the distal end of the device. Although physicians may be instructed to run an implant through the device prior to attempting delivery into a patient tissue pocket, the physician may not actually do so. As a result, the above-described features may not operate because the margin of the tissue pocket can provide adequate support to the sleeve so that it will not rip under unacceptable implant fit situations.

A solution to this problem, then, is to provide a friable feature proximal to the insertion depth of the delivery device. This feature may be discrete/isolated along the length of the sleeve. The feature may comprise an axial and/or longitudinal slit(s) or perforation of the sleeve material, a gap in the tape (if used) to seal the edges of the sleeve or other means. For example, localized weakening of the material can alternatively be accomplished by conditioning the material. The conditioning may comprise an acid etch or exposure to laser, plasma or other energy that results in a change in the properties of the base material.

In another approach, the safety feature runs the length of the sleeve. In which case, the feature may be the bonding tape, with a bond strength selected to fail in shear at a given threshold. Another approach utilizes perforations running the length of the delivery device. Further options are possible as well, as above.

The interior of the sleeve is packaged and supplied with a coating thereon. An example of such coating is hydrophilic coating. It is user-activated by soaking the sleeve in fluid (e.g., deionized water or sterile saline solution) as further described below. It is stably adhered to or bonded to the sleeve. A number of coatings and/or suppliers thereof may supply and/or apply the coating. A preferred vendor is AST Products, Inc. applying LUBRILAST hydrophilic coating and/or other coating(s) as described in U.S. Pat. Nos. 6,238,799 and 6,866,936; other suitable coatings can be applied as well to devices such as the device set forth in the Keller U.S. patent application Ser. No. 12/228,072 filed on Dec. 7, 2007, all of which are incorporated herein by reference in their entireties.

So coated, the interior of the sleeve becomes extremely slippery/lubricous when soaked. The lubricous coating adhered to the sleeve, then, controllably allows the silicone implant to be manipulated down and out of the tapered device into place by a squeezing/pushing motion. Preferably, such motion is applied to the sleeve proximal to the bulk of the implant. Delivering an implant by such action avoids damage to the implant and/or further fuss or fiddle in delivering a pre-filled implant, such as a silicone breast implant.

The construction of the sleeve facilitates preparing it for use in the manner described by allowing compaction of the sleeve into a basin (i.e., a disposable bowl or other undersized container—such as the implant packaging itself—as typically available in an operating room). Specifically, the foldable (vs. merely flexible) nature of the fabric and non-interfering seam provide advantages. These features allow the device to be easily folded, crumpled or otherwise compacted to fit into such a container and at least substantially submerged in fluid without continued manual effort and/or compression under another object to push or hold it down. Moreover, such action (the compaction) is accomplished without damage to the sleeve. Ideally, no significant trace of the sleeve manipulation is evident when the device is put to use. That does not mean that no visual evidence of the manipulation remains. Rather, no structural damage has occurred.

The coating may be applied to the subject device(s) in a number of ways. In one approach, if the end of the sleeve is open, it can be closed-off by an object (such as a ball) and the interior filled with coating fluid that is subsequently poured out. In another approach, the exterior of the sleeve can be masked with a removable layer (e.g., adhered paper or tape) to avoid coating the outer surface when spraying or dip-coating. In another approach, the interior of the sleeve is blocked from receiving coating (e.g., by taping off the ends of the sleeve with double-stick tape or otherwise) and only the exterior of the device is coated. After removing the tape (e.g., by cutting off the sealed/blocked ends), the sleeve is rolled over/everted so that now only the interior surface is coated. In any case, it is desirable to avoid hydrophilic coating on the exterior of the finished device in order to permit better physician grip on the sleeve after its soaking.

The present invention includes such features as described above. Still further, it includes methods associated with and/or activities implicit to the use of the devices described.

BRIEF DESCRIPTION OF THE DRAWINGS

The figures provided herein are not necessarily drawn to scale, with some components and features being exaggerated for clarity. Each of the figures diagrammatically illustrates aspects of the invention. Of these.

Variation of the invention from the embodiments pictured is, of course, contemplated. Moreover, details commonly understood by those with skill in the art may be omitted.

DETAILED DESCRIPTION

Figure 1:
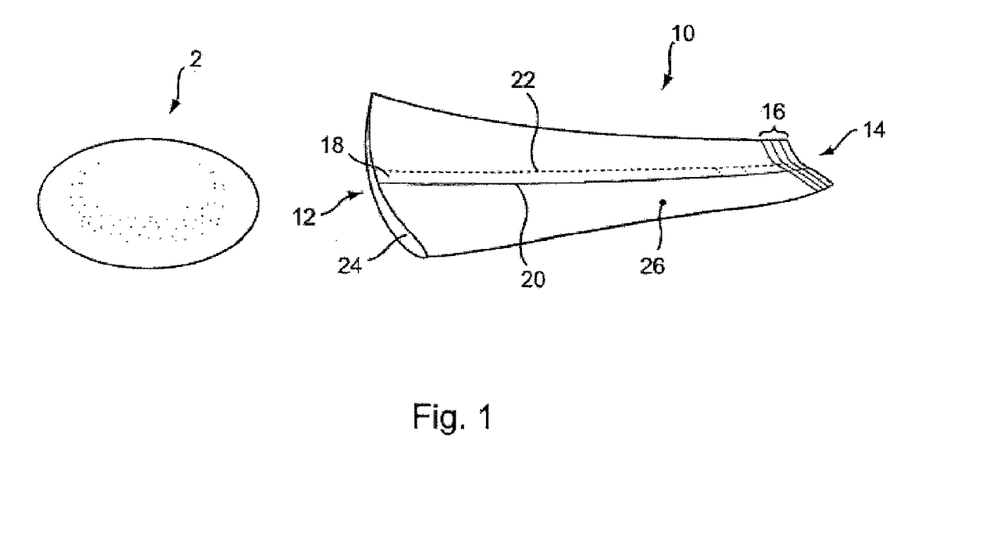
FIG. 1 shows the subject sleeve and a pre-filled implant for delivery therethrough.

FIG. 1 illustrates a pre-filled silicone implant 2 and sleeve 10 according to the present invention provided to facilitate implant delivery. Sleeve 10 has general conical shape that defines a first opening 12 at a larger end and a smaller opening 14 at a terminal end.

The tip of the device may include indicia 16 coordinated to various implant sizes to facilitate trimming the opening to the correct size. The indicia provide a guide for a practitioner to cut along a selected line in order to size the exit diameter of the device for a given implant in a size range, for example, of between about 150 cc to about 800 cc. By so trimming the sleeve, exit diameters from between about 3 cm to about 6 cm are provided. For a more typical range of implant sizes, the openings may be sized approximately as follows (width dimension measured with the sleeve laid flat): 4.5 cm for 300 cc implants, 5.0 cm for 300 cc to 450 cc implants, and 5.5 cm for 450 cc to 550 cc implants.

Figure 2A:
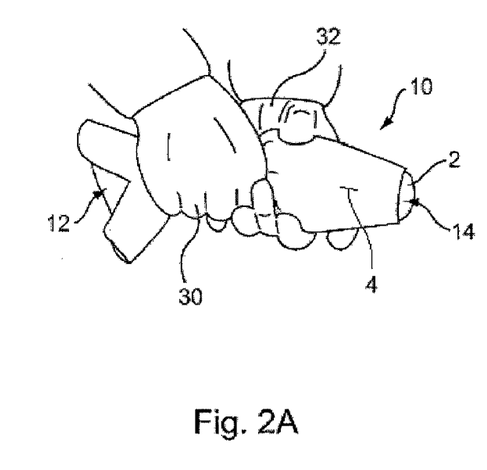
FIGS. 2A and 2B illustrate manipulation of the sleeve.
Figure 2B:
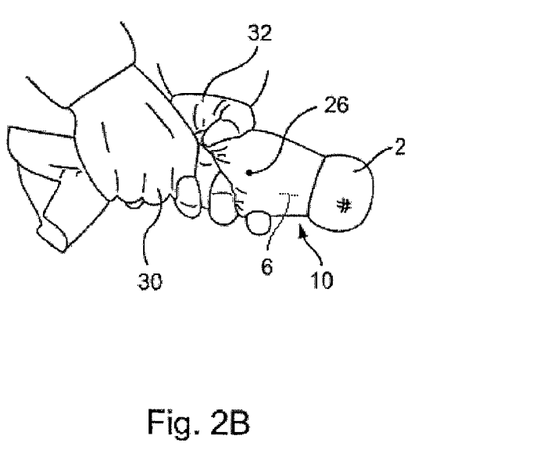

Sleeve 10 is advantageously constructed with a seam 18 formed using double-sided tape to close overlapping edges 20, 22 of a cut sheet. Of course, other joining methods (e.g., ultrasonic welding), and/or constructional approaches may be employed. Seam 18 may have a gap or break (e.g., between sections of the tape, as indicated by a dashed line) in it to provide a friable safety feature. The tape may terminate proximal of the distal end for the same purpose. As shown in FIGS. 2A and 2B, another approach includes a slit 4 or perforated section 6 in sleeve 10. In order that the tissue pocket not interfere with the operation of such a feature, it should be located at least about 2-3 cm, more typically at least about 5 cm, proximal to the distal edge 8 of the sleeve.

Apart from such optional aspects, sleeve 10 necessarily includes a user-activated lubricious coating 24 adhered to the interior of the sleeve. So coated, no introduction of further lubricant into the sleeve or over the surface of the implant is required for implant delivery. Instead, coating 24 is stably adhered to the sleeve, and simply activated (e.g., by hydration) for use. Such a coating substantially mitigates or altogether eliminates risk associated with the introduction of additional foreign body material (in the form of applied lubricant) into the patient along with the implant.

Given that lubricant need not be applied to the surface of the implant and that the implant is neither directly manipulated during delivery nor introduced in such a way that it touches the recipient's skin, the implantation procedure may proceed as a "no-touch" approach. Such an approach is advisable in avoiding capsular contracture.

Capsular contracture is an abnormal response of the immune system to foreign materials. The exact cause of contracture is not known. However, noted factors include bacterial contamination, silicone breast implant rupture or leakage, and hematoma. Methods which have reduced capsular contracture include limiting handling of the implants and skin contact prior to insertion as well as irrigation with triple-antibiotic solutions. Use of the present invention easily enables practicing these methods and further addresses the noted factors as a gentle, no-touch means of implant delivery.

As shown in FIGS. 2A and 2B, when an implant 2, such as a silicone implant, is set into sleeve 10, the sleeve can be manipulated to apply pressure to direct the implant along the length of the sleeve and toward distal opening 14. The flexible sleeve is conformed to the implant where there is slack in the material, and the implant to the sleeve where sleeve material is taut. The larger proximal opening 12 of the sleeve allows for implant introduction into the sleeve with little or substantially no digital force or manual manipulation.

With the implant set within the sleeve, the sleeve body 26 may be twisted closed. By any combination of such twisting and progressive compression action (such progression illustrated in transition from FIG. 2A to FIG. 2B) the surgeon is able to apply pressure via the sleeve to the implant and force it out of the delivery device and into a surgical pocket as illustrated in subsequent figures. Generally, a proximal hand 30 grip is used primarily to drive the implant forward, with the distal hand 32 grip more for offering stability and guidance to the end of the sleeve.

In addition, when introducing the implant into a surgical pocket, the pocket can be manipulated by a retractor to force the pocket open. Such action opens the void/space into which the implant is to be set, and may further help draw the implant inward by creating a partial vacuum. Moreover (although by no means necessary), the retractor may next be brought to bear on the sleeve to further assist the user's manipulation of the sleeve to extrude the implant into the surgical pocket.

Figure 3A:
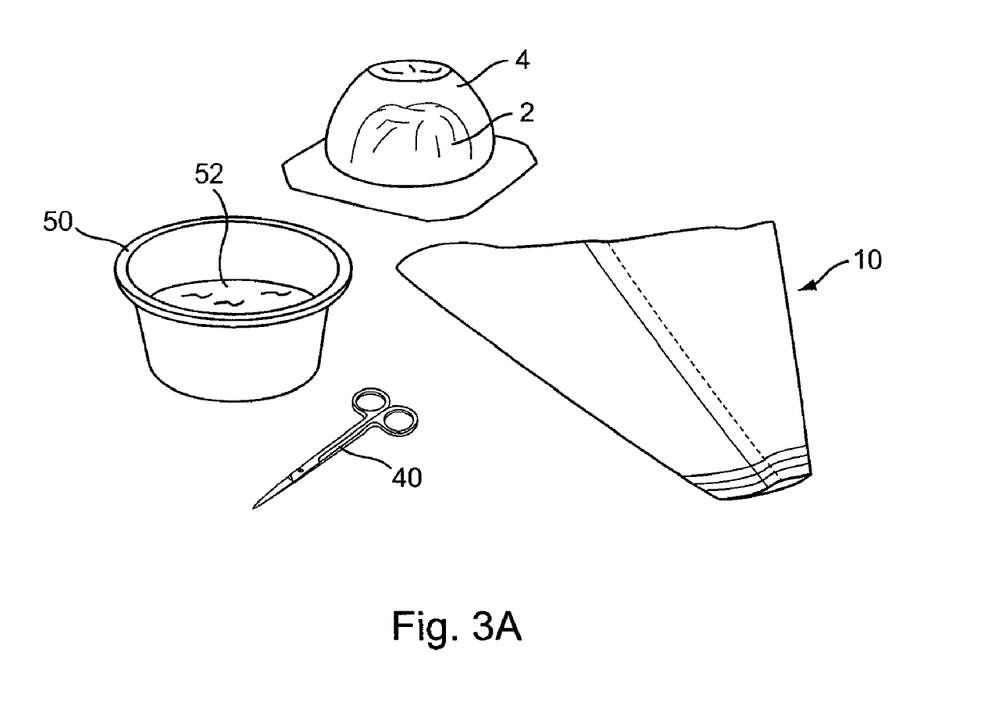
FIG. 3A-3F illustrate preparatory acts in using the subject device.
Figure 3B:
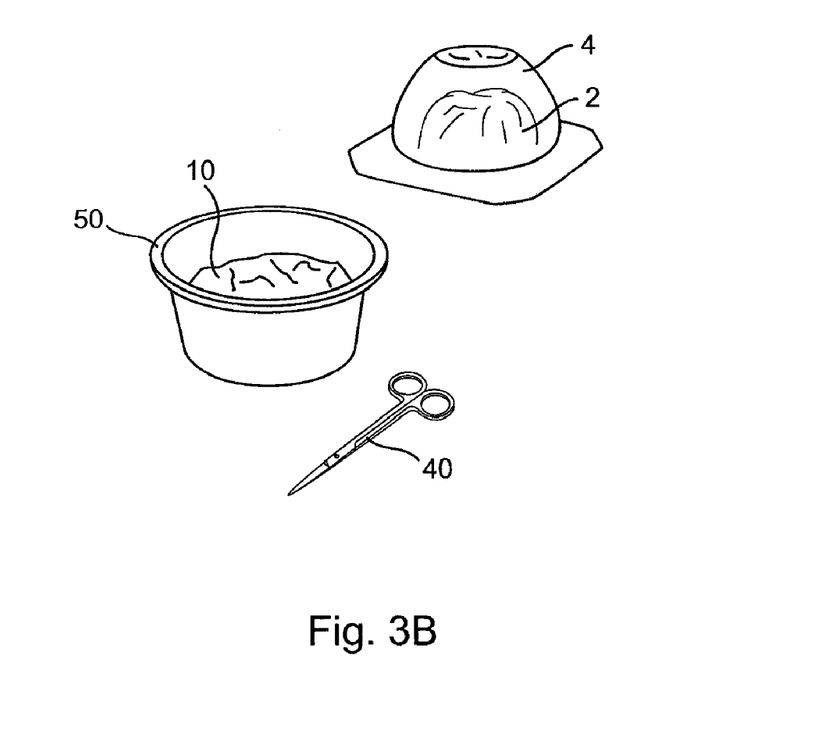

FIGS. 3A-3F offer more detail regarding use of the subject delivery sleeve. Specifically, this series of figures illustrates the manner in which the sleeve and an implant are prepared. FIG. 3A shows each an implant 2 in its packaging 4, the sleeve 10 (removed from sterile packaging), scissors 40, and a basin 50 as typically found in a surgical suite. The basin is shown partially filled with saline 52 (optionally including antibiotic solution and/or Betadine®). To activate the lubricious coating inside the sleeve, the sleeve is folded or simply pushed into basin 50 in a compacted state as shown in FIG. 3B to soak. The sleeve preferably remains in fluid until time for use.

Figure 3C:
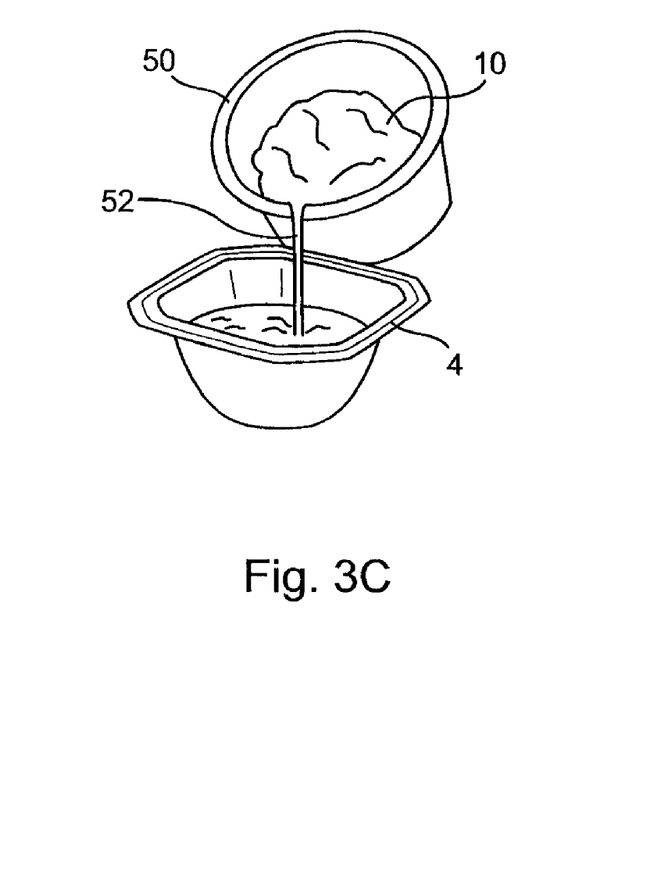

At least some of the fluid in the basin can be poured off into the implant packaging container 4 as shown in FIG. 3C in order to bathe the implant in solution (especially useful if loaded with antibiotics) prior to implantation.

Figure 3D:
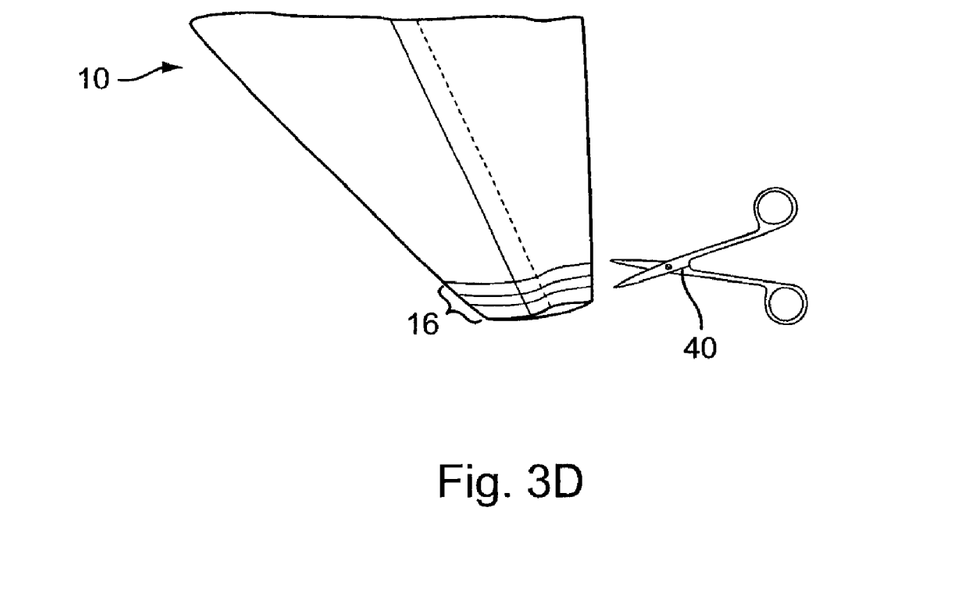

If trimming the sleeve end is desired in order to better fit a specific implant size, it may occur next as illustrated in FIG. 3D. However, sleeve 10 may be trimmed as soon as it is unpackaged. Alternatively, the delivery sleeve may be specifically sized and/or packaged in coordination with a given size of implant to avoid any such need. Proper implant-to-sleeve sizing is ensured in either case by the fail-safe feature of the present invention, for example, as described above.

Figure 3E:
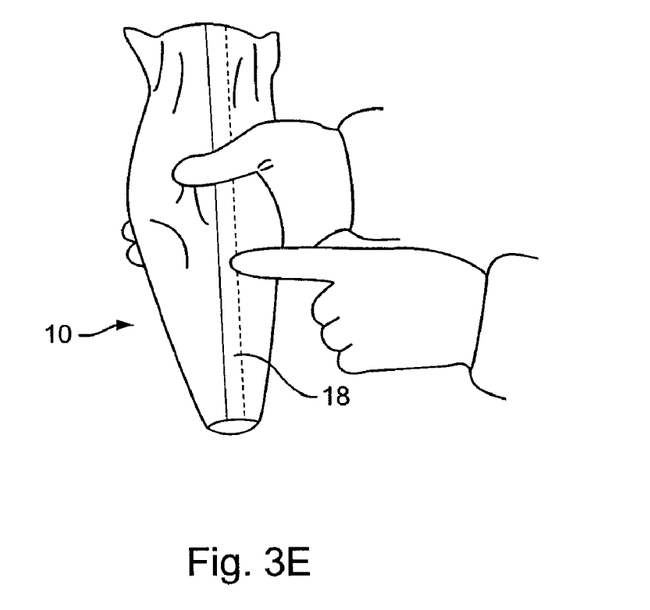
Figure 3F:
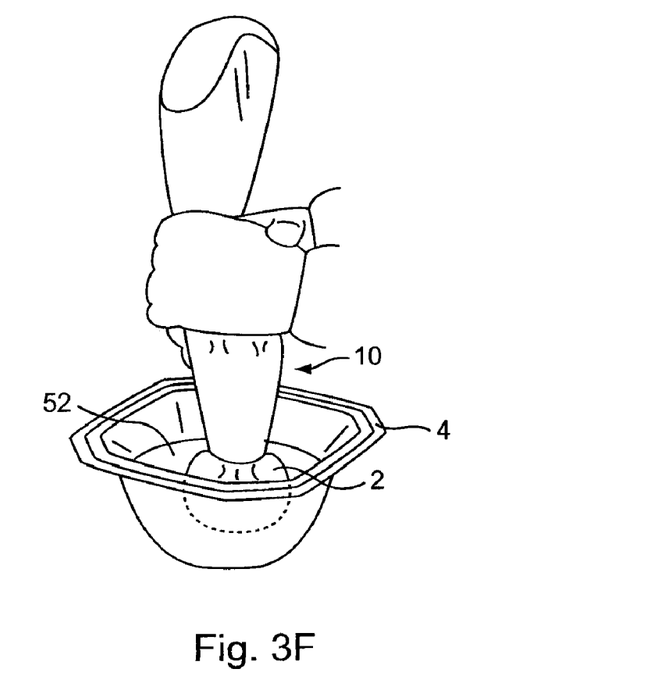

FIG. 3E illustrates the sleeve 10 with an implant therein. Because of the translucent nature of the sleeve material, implant orientation can be visually confirmed as indicated in relation to the landmark offered by the tape seam 18. Prior to delivering the implant in a medical procedure, a test run may be performed as illustrated in FIG. 3F by running the implant through the sleeve. Performing such a test run offers a valuable fit check, especially when the sleeve end had been trimmed to accommodate larger-sized implants to ensure that the implant will push-out cleanly.

At this point, the sleeve will tear or split if the implant is oversized relative to the delivery end. If so, a new sleeve is obtained, and trimmed to a larger size end opening. If successfully passed through the sleeve, however, the implant is re-loaded in the sleeve for implantation deployment.

FIGS. 4A-4D illustrate use of the subject device in delivering an implant employing a transaxillary approach. An incision 60 is created in an axillary site leading to a subcutaneous pocket (not shown) under left breast 62. The pocket may be formed by employing various dissection techniques known to skilled practitioners. The access incision is shown held open by a small retractor 42. The pocket itself may be created in either the subglandular or subpectoral space. The submuscular plane tends to be less vascular, and is associated with fewer sensory alterations of the nipple areolar complex. So, a subpectoral pocket may be preferred.

Figure 4:
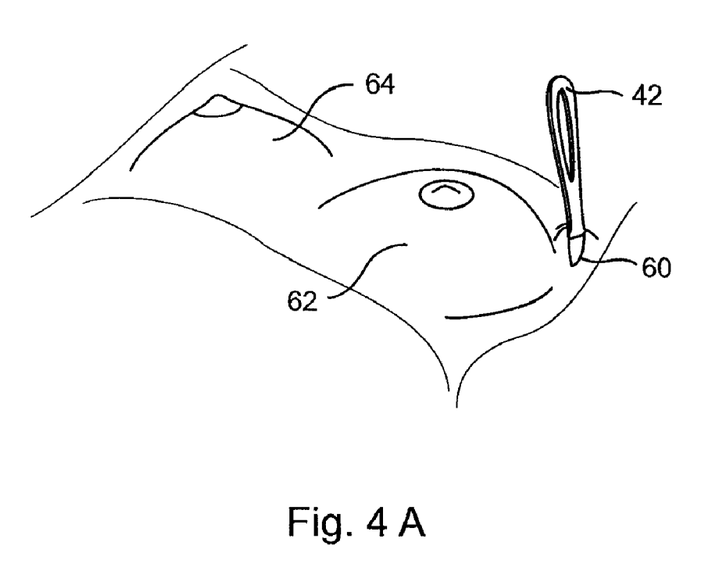
FIGS. 4A-4D illustrate use of the present invention in a breast augmentation procedure.
Figure 4C:
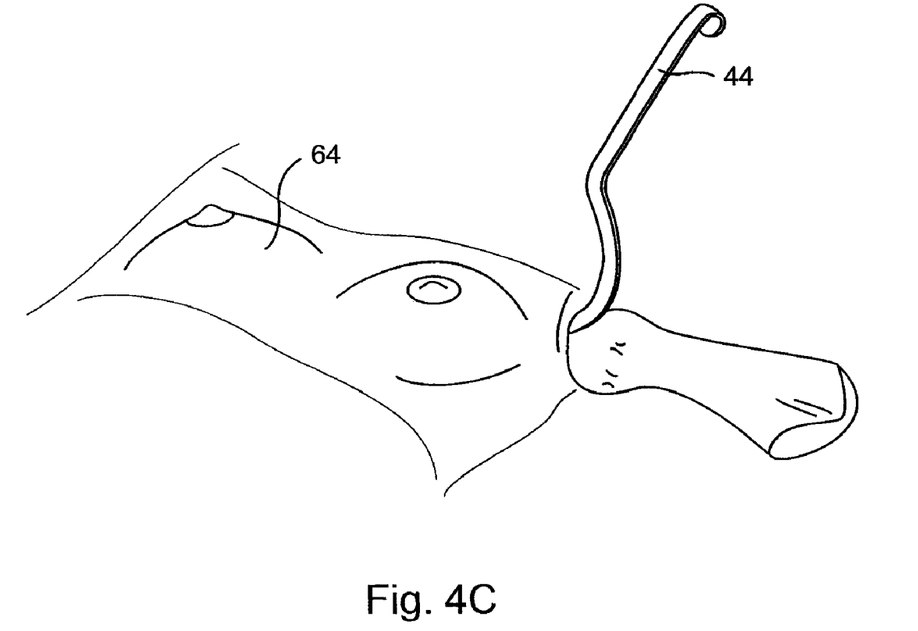

In any case, FIG. 4B illustrates a larger Deaver retractor 44 passing through incision 60 into the breast pocket. In addition, the distal tip of sleeve 10 is received within the incision. As shown in FIG. 4C, while the implant is squeezed forward along the sleeve, the retractor may be used to urge the surgical pocket open and/or bear down on the sleeve as described above.

Figure 4D:
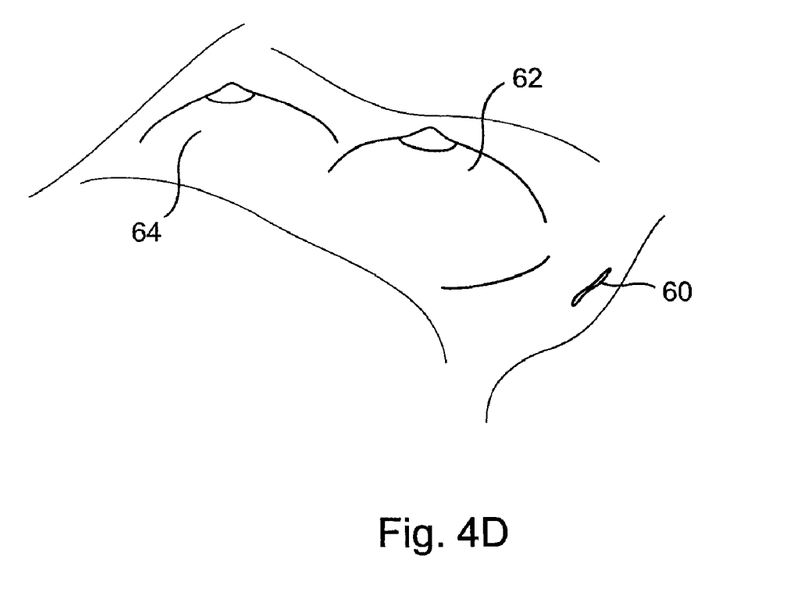

FIG. 4D illustrates left breast 62 enlarged as desired. Once right breast 64 is similarly treated and symmetry confirmed (with any subsequent adjustments made), the breast pocket incisions are closed.

Figure 5A:
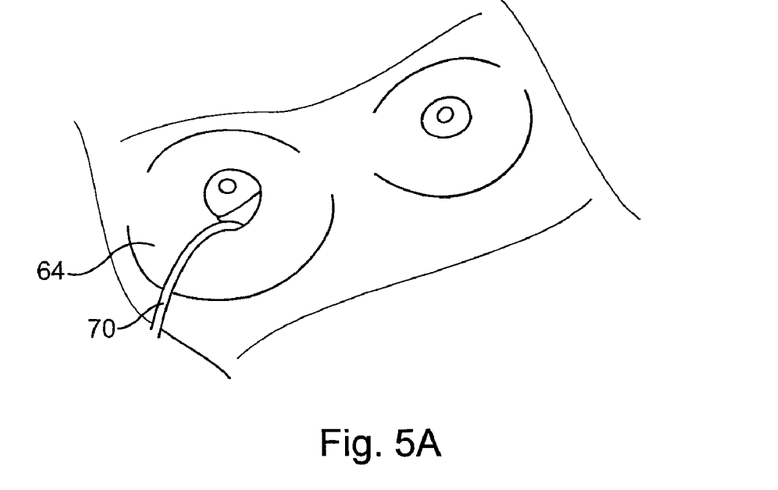
FIGS. 5A-5D illustrate use of the present invention in an alternative surgical approach for breast augmentation.
Figure 5B:
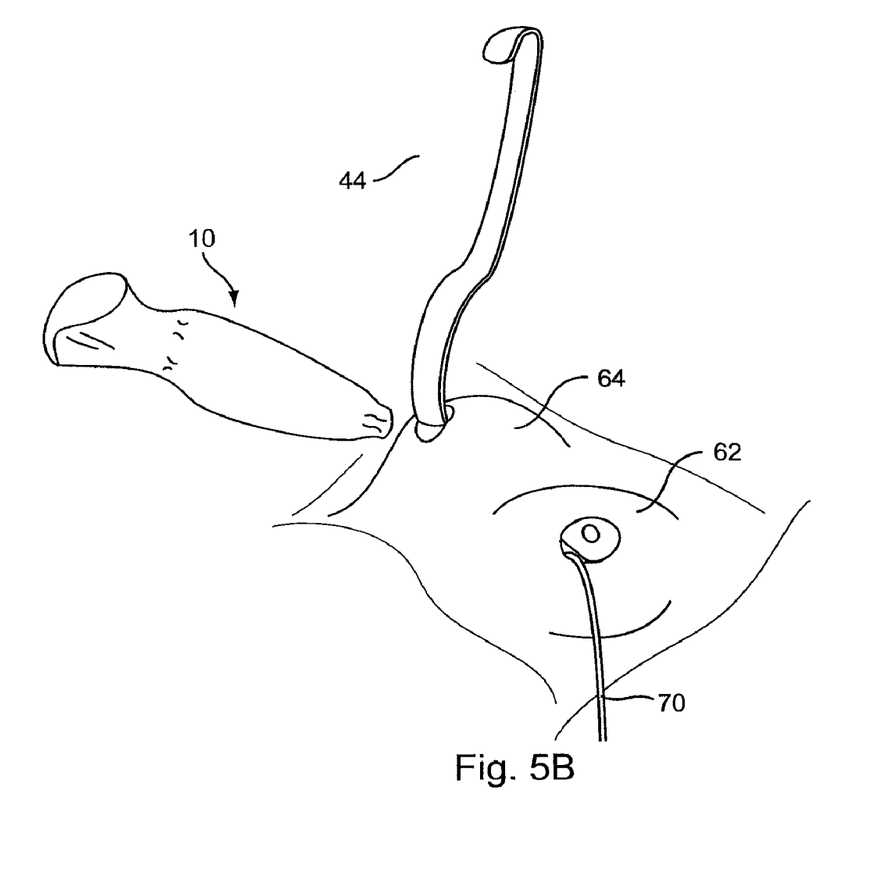

Note, prior to undertaking implant delivery, an inflatable sizer will typically be placed in the pocket under each breast. These sizer(s) may be placed to aid in prosthesis size selection, and can also be over-filled to provide intraoperative tissue expansion. FIG. 5A illustrates a first sizer emplaced using a periareolar approach (sizer fill tube 70 shown). With a second sizer in place, FIG. 5B shows the Deaver retractor 44 inserted into the right breast 64 pocket and sleeve 10 being introduced into the incision. In doing so, the tip or distal end of the sleeve may be crimped or crumpled down as shown to aid in passing through the incision.

Indeed, the same technique may be employed irrespective of access approach chosen. However, the technique may be more helpful or necessary for introduction into smaller incisions.

Figure 5C:
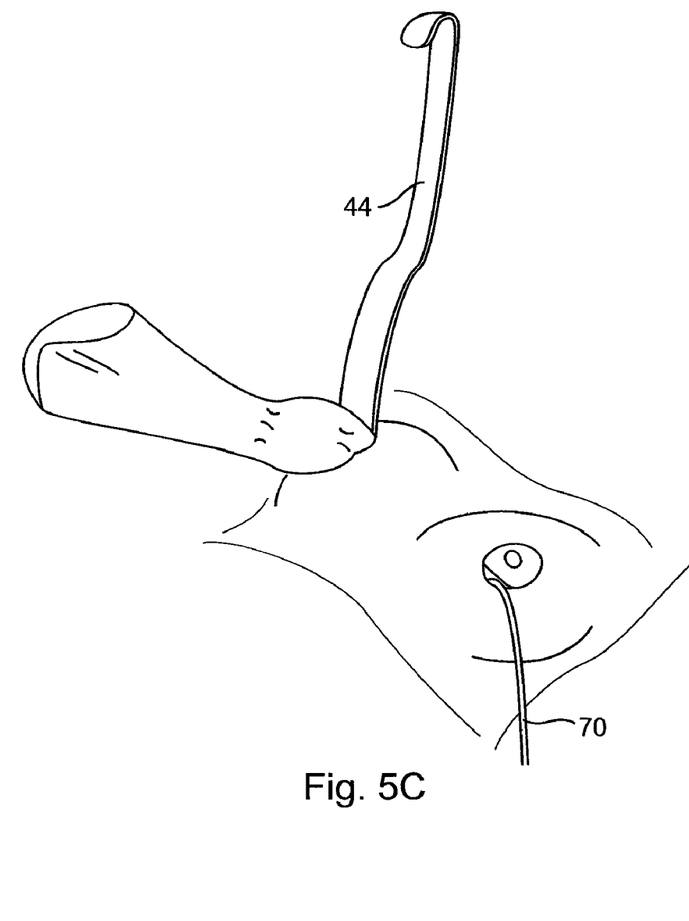
Figure 5D:
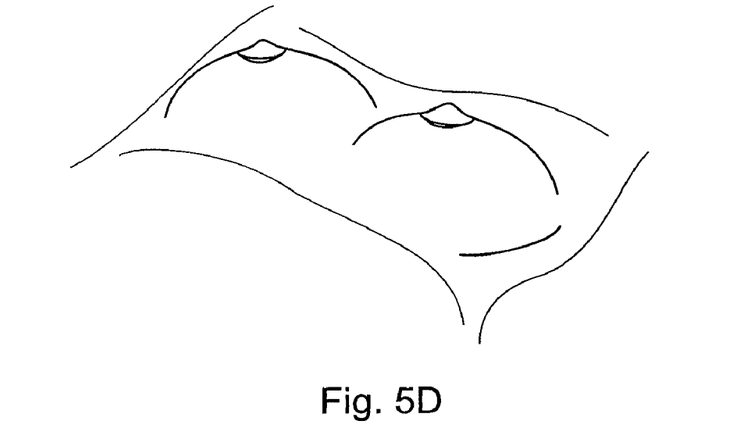

FIG. 5C illustrates implant extrusion into the breast pocket much as shown in FIG. 4C. A complete augmentation procedure (save final incision closure) in which both breasts 62 and 64 are filled is presented in FIG. 5D.

Regardless of the surgical approach taken, it has been found that the step of inserting a pre-filled silicone implant can occur within a timeframe of about 5 to about 20 seconds employing the subject invention as compared to a time interval of up to 5 to 15 minutes for a traditional hand manipulation of the same implant. Additionally, because the implant can be inserted through a small opening, the size of the surgical incision can be made smaller than would otherwise be required for a silicone implant. Essentially, saline implant-size incisions can effectively be used to deliver pre-filled silicone implants.

Illustrative examples of such use under confidential clinical site conditions include:

| Incision Site | Implant Style | Sleeve Opening Size (cm)* | Exterior Incision Size (cm) | | Silicone Breast Implant Volume (cc) | |
|---|---|---|---|---|---|---|
| | | | Left | Right | Left | Right |
| Axillary | Moderate Plus | 4.5 | 3.2 | 3.5 | 275 | 300 |
| Periaerolar | Moderate Plus | 6.0 | 5.0 | 5.0 | 550 | 550 |
| Periaerolar | Moderate Plus | 5.5 | 5.5 | 5.5 | 400 | 400 |
| Periaerolar | Moderate Plus | 6.0 | 4.0 | 4.0 | 400 | 400 |
| Periaerolar | High Profile Smooth Round | 5.5 | 3.0 | 3.5 | 500 | 500 |

*Opening Size measured when sleeve is laid flat on table.

Viewed otherwise, a larger silicone implant can be delivered for a given incision size as will be appreciated by those with skill in the art. Such a consideration may be important especially when considering a periareolar approach as illustrated in FIGS. 5A-5D.

The periareolar approach may sometimes be preferred because the color of the areola can offer "camouflage" to help the incision scar blend in. The periareolar approach is often less surgically challenging than a transaxial approach. But since the size of the incision is coordinated with that of the areola in a periareolar approach, the size of the pre-filled implant that could previously be inserted therethrough is sometimes limited. Use of the subject device relaxes this limitation, thereby offering both the patient and surgeon more (often better) options.

The invention includes the methods set forth above in terms of method of manufacture, preparation and/or use. The methods may be performed using the subject devices and sometimes by other means.

The methods may include the act of providing a suitable device. Such provision may be performed by the end user. In other words, the act of "providing" merely requires that the end user access, approach, position, set-up, grasp or otherwise obtain the requisite device for the subject method. Methods recited herein may be carried out in any order of the recited events which is logically possible, as well as in the recited order of events.

Exemplary aspects of the invention, together with details regarding material selection and manufacture, have been set forth above. As for other details of the present invention, these may be appreciated in connection with the above-referenced patents and publications as well as generally known or appreciated by those with skill in the art. The same may hold true with respect to method-based aspects of the invention in terms of additional acts as commonly or logically employed.

In addition, though the invention has been described in reference to several examples, optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range is encompassed within the invention.

Also, it is contemplated that any optional feature of the inventive variations described may be set forth and claimed independently, or in combination with any one or more of the features described herein. Stated otherwise, it is to be understood that each of the improvements described herein independently offers a valuable contribution to the state of the art. So, too, do the various other possible combinations of the improvements/features described herein and/or incorporated by reference, any of which may be claimed.

Reference to a singular item, includes the possibility that there are plural of the same items present. More specifically, as used herein and in the appended claims, the singular forms "a," "an," "said," and "the" include plural referents unless specifically stated otherwise. In other words, use of the articles allow for "at least one" of the subject item in the description above as well as the claims below. It is further noted that the claims may be drafted to exclude any optional element. As such, this statement is intended to serve as antecedent basis for use of such exclusive terminology as "solely," "only" and the like in connection with the recitation of claim elements or use of any "negative" limitation.

Without the use of such exclusive terminology, the term "comprising" in the claims shall allow for the inclusion of any additional element—irrespective of whether a given number of elements are enumerated in the claim, or the addition of a feature could be regarded as transforming the nature of an element set forth in the claims. Except as specifically defined herein, all technical and scientific terms used are to be given as broad a commonly understood meaning as possible while maintaining claim validity.

The invention claimed is:

1. An apparatus for inserting a pre-filled prosthesis into a surgical pocket, the apparatus comprising:
   a compactable, tapered sleeve, open at both proximal and distal ends for use,
   the sleeve including a feature adapted to tear before damage to the implant occurs when forcing the implant through the distal end for insertion into the surgical pocket.

2. The apparatus of claim 1, wherein the feature is provided by constructing the sleeve from rip-stop nylon fabric between about ¾ to about 1½ oz weight per sailmaker's yard.

3. The apparatus of claim 1, wherein the feature is provided by a gap in a seam between sections of the sleeve.

4. The apparatus of claim 1, wherein the feature is provided by a slit in a material defining the sleeve.

5. The apparatus of claim 1, wherein the feature is provided by perforations in a material defining the sleeve.

6. The apparatus of any of claims 3-5, wherein the feature is provided at least about 5 cm proximal to a distal edge of the sleeve.

* * * * *